(12) United States Patent
Wetzel

(10) Patent No.: US 9,389,131 B2
(45) Date of Patent: Jul. 12, 2016

(54) FIBER SNUBBING CLAMP USING MAGNETIC GRIPPING ACTION

(71) Applicant: U.S. Army Research Laboratory, Washington, DC (US)

(72) Inventor: Eric D. Wetzel, Baltimore, MD (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 8 days.

(21) Appl. No.: 14/228,783

(22) Filed: Mar. 28, 2014

(65) Prior Publication Data

US 2014/0208862 A1     Jul. 31, 2014

Related U.S. Application Data

(62) Division of application No. 13/415,121, filed on Mar. 8, 2012, now Pat. No. 8,991,263.

(60) Provisional application No. 61/450,309, filed on Mar. 8, 2011.

(51) Int. Cl.
    *G01L 5/04*           (2006.01)
    *B25B 11/00*        (2006.01)
    *G01N 3/04*          (2006.01)
    *G01N 3/08*          (2006.01)

(52) U.S. Cl.
CPC .................. *G01L 5/04* (2013.01); *B25B 11/002* (2013.01); *G01N 3/04* (2013.01); *G01N 3/08* (2013.01); *G01N 2203/028* (2013.01)

(58) Field of Classification Search
CPC ................................ G01L 5/04; B25B 11/002
USPC ............................................................ 73/828
See application file for complete search history.

(56) References Cited

U.S. PATENT DOCUMENTS

| | | | |
|---|---|---|---|
| 6,679,124 B2 * | 1/2004 | Oliver .......................... 73/796 |
| 2007/0036508 A1 * | 2/2007 | Sato ............................. 385/137 |
| 2008/0210014 A1 * | 9/2008 | Merendino .................... 73/818 |
| 2010/0270350 A1 * | 10/2010 | Bylander et al. ................. 225/2 |
| 2014/0003785 A1 * | 1/2014 | Sato ............................. 385/137 |

OTHER PUBLICATIONS

ASTM Standard D 3822-07. "Standard Test Method for Tensile Properties of Single Textile Fibers." ASTM International, West Conshohoken, PA. 2007.

(Continued)

*Primary Examiner* — Lisa Caputo
*Assistant Examiner* — Jamel Williams
(74) *Attorney, Agent, or Firm* — Christos S. Kyriakou

(57) ABSTRACT

A device, assembly and method for clamping single fibers that utilizes snubbing surfaces simultaneously with magnetic gripping action are described. The device can be fabricated at miniature sizes with very low mass and volume, which are desirable requirements for testing of small fibers in highly sensitive force-transducing load frames. Advantageously, the combined use of snubbing surfaces and magnetic gripping greatly reduces the probability of slippage or fiber failure at the grip during testing.

24 Claims, 8 Drawing Sheets

(56) References Cited

OTHER PUBLICATIONS

J. Scott Thornton, Sam R. Allen, and Shawn L. Arnett. "Effect of Gripping Technique on Tensile, Tensile Creep and Tensile Creep-Rupture Results for a High Tenacity Polyester Yarn." In Grips, Clamps, Clamping Techniques, and Strain Measurement for Testing of Geosynthetics. P. E. Stevenson, Ed. ASTM STP 1379. ASTM International, West Conshohoken, PA. p. 47-67. 2000.

ASTM Standard D 885-04. "Standard Test Methods for Tire Cords, Tire Cord Fabrics, and Industrial Filament Yarns Made from Manufactured Organic-Base Fibers." ASTM International, West Conshohoken, PA. 2004.

\* cited by examiner

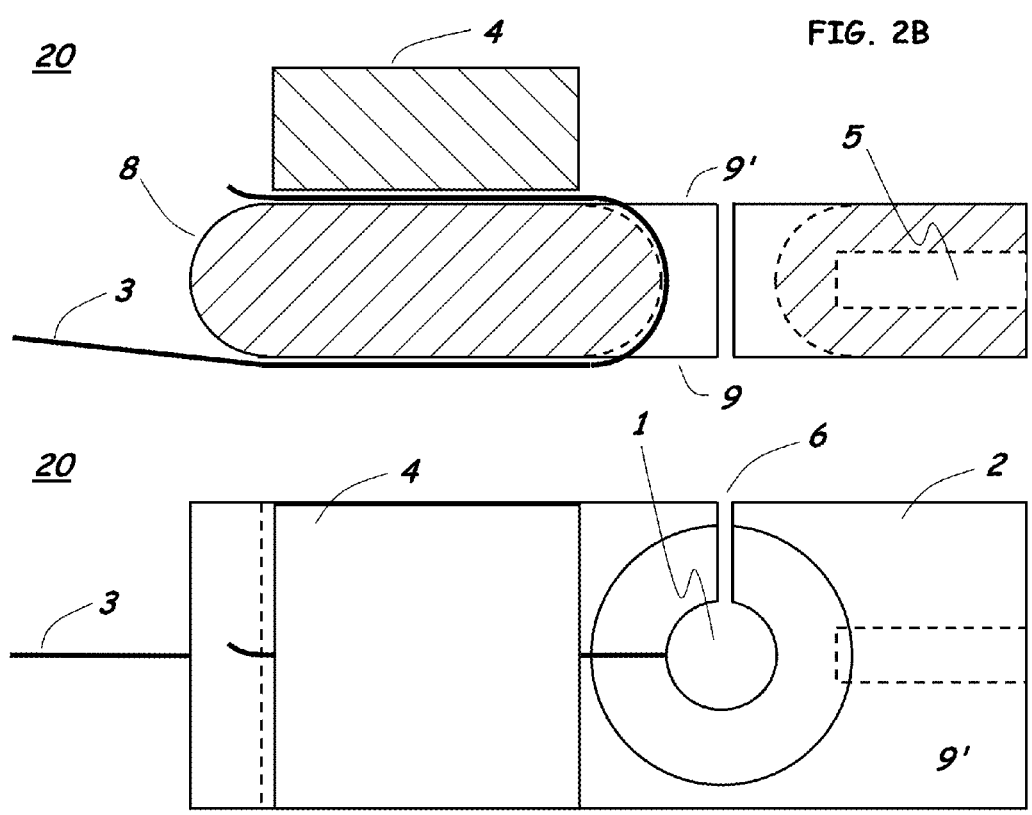

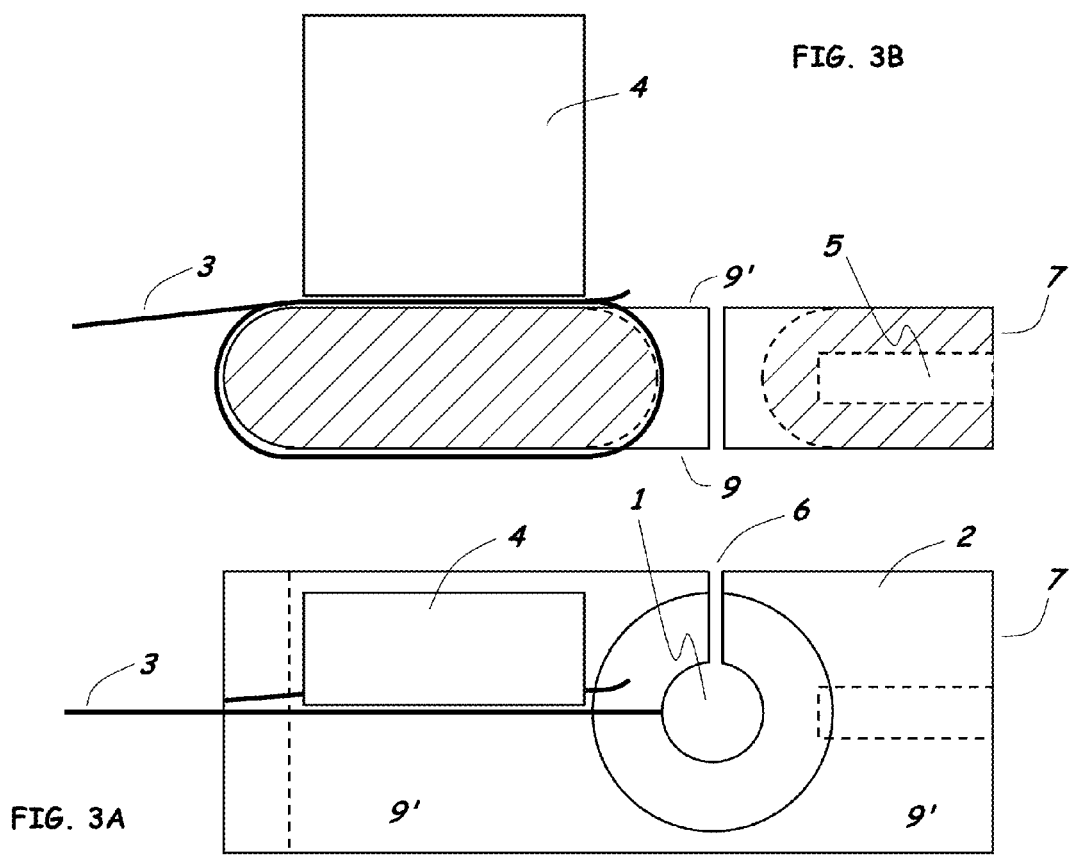

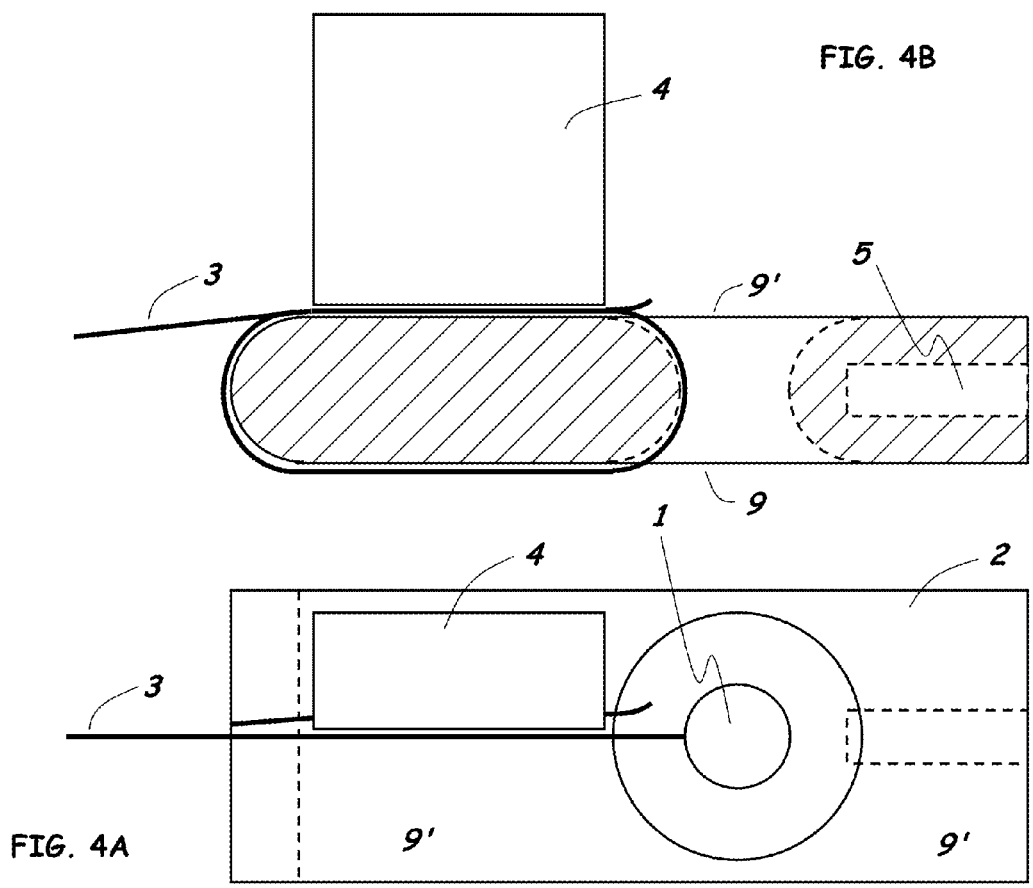

FIG. 7B
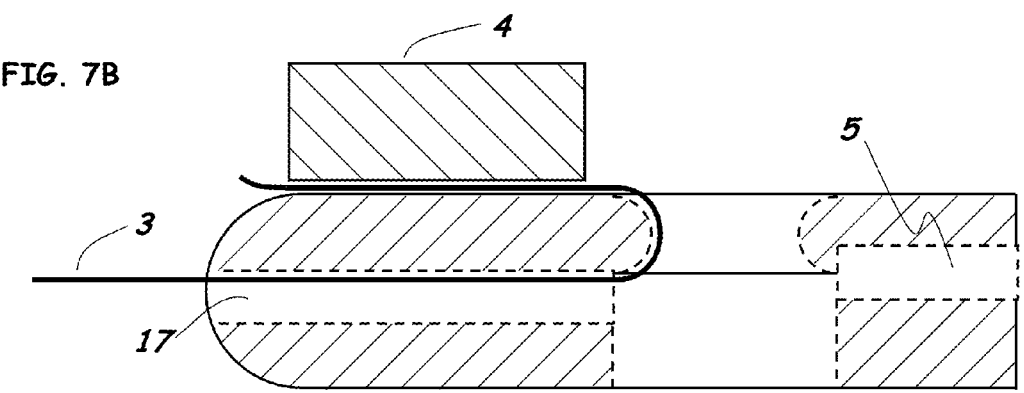
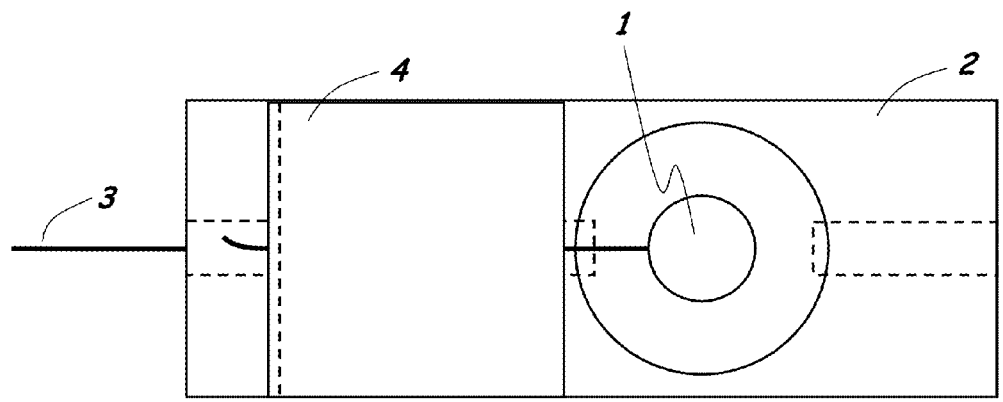
FIG. 7A

FIBER SNUBBING CLAMP USING MAGNETIC GRIPPING ACTION

CROSS-REFERENCE TO RELATED APPLICATIONS

This application is a divisional of U. S. patent application Ser. No. 13/415,121 filed Mar. 8, 2012 titled, "Fiber Snubbing Clamp Using Magnetic Gripping Action" and claims benefit of U.S. Provisional application No. 61/450,309 titled "Single Fiber Snubbing Clamp Using Magnetic Gripping Action" filed on Mar. 8, 2011 which are both hereby incorporated by reference herein.

GOVERNMENT INTEREST

The invention described herein may be manufactured, used, and licensed by or for the United States Government.

BACKGROUND OF THE INVENTION

The ability to test the tensile strength and other mechanical properties of single fibers is of great importance for researchers, engineers, and manufacturers. Single fiber testing can be used to isolate trends and modes of failure for materials, such as for fundamental materials investigations or product-line quality control testing. During development of new fiber materials, the new fibers are often available in very small quantities due to complex processing or exotic materials. In these cases, multi-filament yarn-level testing is not practical. Instead, it is desired to generate mechanical properties of individual filaments.

Developments in capacitive load cells, electromagnetic load cells, and stepper motor technology have led to the commercialization of compact load frames with extremely sensitive force (for example, nanoNewton (nN) sensitivity) and displacement (for example, nanometer (nm) sensitivity) measurement capabilities. These miniature load frames are ideally suited for testing single fibers.

Standard testing procedures for single fibers[1] call for directly gripping single fibers in clamping action grips, or gluing the fibers onto cardboard tabs that are then gripped in clamping action grips. The first technique, direct clamping, concentrates stresses at the grip point and often leads to failure at the fiber grips[2]. Grip failure is undesirable during fiber characterization, and these results are generally not accurate, and, thus, are not reportable. The second technique, bonding fibers onto cardboard tabs, relies on strong bonding between the fiber and a dollop of adhesive. For fibers that are difficult to bond to, such as aramid, polyethylene, or ultrahigh molecular weight polyethylene, it is common to observe fiber slippage from the adhesive. These results are also not accurate and, thus, are not reportable, and generally prevent loading the fiber to failure. In addition, the time and complication associated with utilizing curable adhesives adds considerable inconvenience, especially considering that many test repetitions are required to establish statistically significant data. Accordingly, there is a need for a method, a device and/or an assembly for clamping or otherwise securing a fiber in a tensile testing device.

For testing yarns, it is common to use capstan grips (also called roller grips) or contour/horn grips (also called half-capstan grips)[2,3]. In these designs, from the primary loading gage section of the yarn the yarn is passed over a series of "snubbing" surfaces which gradually reduce the tensile load on the yarn due to frictional interactions of the yarn with the snubbing surfaces. The snubbing surfaces are curved gently to induce normal forces on the yarn without creating stress concentrations that can fail the yarn. After passing over these snubbing surfaces, the yarn is gripped mechanically, typically using mechanical or pneumatic clamping action. Because the tensile loading on the yarn has been gradually reduced, the total stress on the yarn at the grip point is significantly less likely to lead to failure at the grip.

The present invention improves upon previous single fiber techniques by providing a single fiber clamping device that can reliably grip single fibers and decrease slippage and/or failure at the grips. In addition, no adhesive is required, so that gripping is fast and uncomplicated. Furthermore, the device uses magnetic clamping action to grip the fibers, so that the total mass and volume of the clamping device are minimized. Maintaining low clamping device mass is desirable for operation in sensitive load frames, since the total load limits (including clamp weight) are typically very low for these miniature load frames (for example, 1 N maximum force capacity). For these applications, traditional clamping approaches such as mechanical action or pneumatics are undesirable because they are either impractical or cumbersome to implement.

SUMMARY OF THE INVENTION

The present invention is a single fiber clamping device that utilizes capstan style snubbing surfaces to gradually reduce fiber tension as it approaches the clamping point, similar to the capstan-style grips used for testing of yarns. Magnetic forces are used to provide the clamping action on the fiber after the snubbing surfaces. The geometry of the device can be optimized for compactness, low mass, and manufacturability.

In addition, a method for determining a mechanical property of a fiber or a yarn or other group of fibers is provided.

BRIEF DESCRIPTION OF THE DRAWINGS

A better understanding of the present invention will be had upon reference to the following detailed description when read in conjunction with the accompanying drawing, wherein like reference characters refer to like parts throughout the several views, and in which:

FIG. 2A is a plan view of another exemplary device of the present invention;
FIG. 2B is a cross-section view of the device of FIG. 2A;
FIG. 3A is a plan view of an exemplary method of the present invention;
FIG. 3B is a cross-section view of the method of FIG. 3A;
FIG. 4A is a plan view of another exemplary method of the present invention;
FIG. 4B is a cross-section view of the method of FIG. 4A;
FIG. 7A is a plan view of yet another device and another exemplary method of the present invention;
FIG. 7B is a cross-section view of the method of FIG. 7A.

DETAILED DESCRIPTION OF PREFERRED EMBODIMENTS

Figures 1A, 1B:
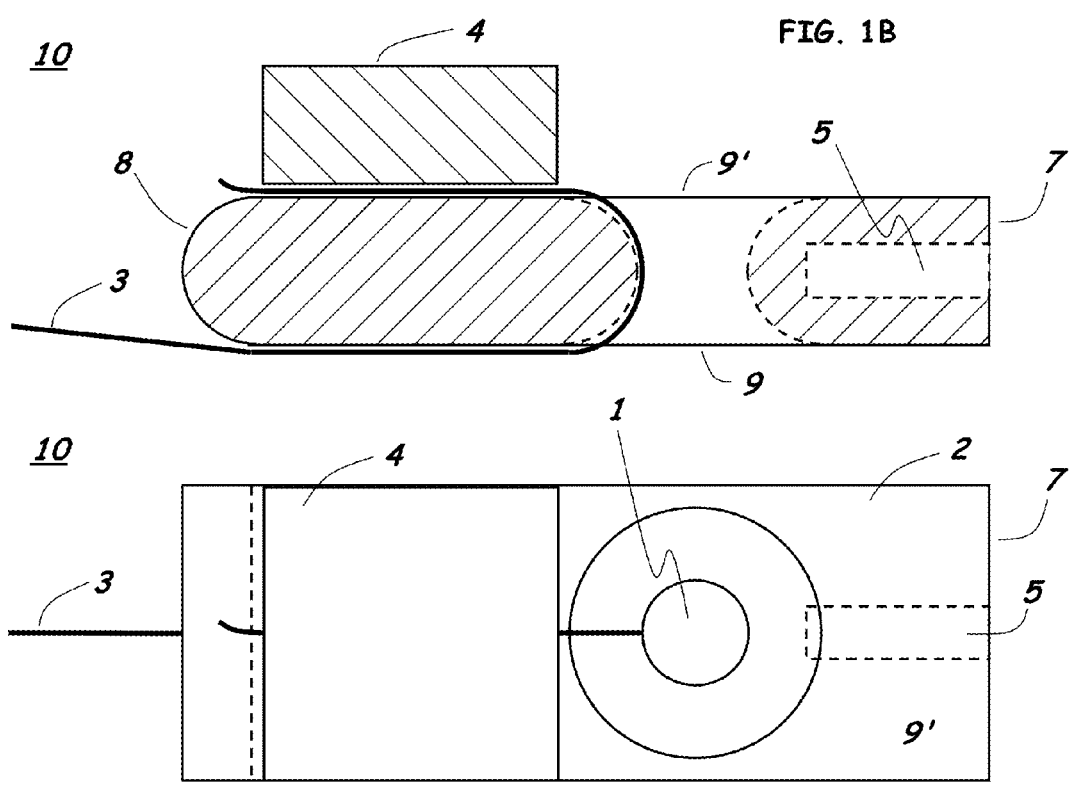
FIG. 1A is a plan view of an exemplary device of the present invention.
FIG. 1B is a cross-section view of the device of FIG. 1A.

FIG. 1A illustrates a plan view and FIG. 1B illustrates a cross-sectional view of one exemplary embodiment of device of the present invention. The exemplary device is a device that can be used to grip an individual fiber and, thus, test the tensile strength of the single fiber on a testing system and device, for example the testing system described in U.S. Pat. No. 6,679,124 to MTS Systems which is hereby incorporated by reference herein. In certain embodiments, two devices of the present invention can be used to replace the upper specimen holder and lower specimen holder, items designated as 14A and 14B, respectively, in FIG. 1 of the material testing system 10 illustrated in U.S. Pat. No. 6,679,124.

An assembly of the present invention includes two devices, for example an upper specimen holder and a lower specimen holder, where each device includes a base 2. A feature of base 2 is a toroidally contoured hole 1. Hole 1 may be machined into base component 2. Desirably, base 2 is composed of or otherwise includes a magnetizable alloy, for example an alloy or metal that will attract a magnet such as free-machining steel. The base may include only a surface portion that includes or is composed of a magnetizable alloy so that at least a portion of a surface of base 2 can be used to attract a magnet. A fore edge 8 of the base 2 device 10 is desirably machined to a rounded, semi-cylindrical contour. To grip a fiber 3, a fiber from the gage direction of a testing system is passed over a portion of first face 9 of base 2 through the hole 1. The fiber 3 is then passed over a second face 9' of base 2 and routed back towards the gage direction. A smooth, low mass clamping magnet 4, such as a polished rare earth permanent magnet, is then placed on top of the fiber 3. In certain embodiments the magnet can be an electromagnet or a non-metallic ceramic magnet. The magnetic attraction of the clamping magnet 4 to a surface of the base component 2 provides clamping action. A threaded rod (not illustrated) is mounted to the aft edge 7 of the base component via a threaded hole 5. The threaded rod can then be mated to the load frame using standard mechanical hardware.

FIGS. 2A and 2B illustrate a plan view, a top view and a cross-sectional view of an alternate embodiment of an assembly 20 of the present invention. The base 2 illustrated in FIGS. 2A and 2B includes a slot 6 that connects a side edge of base 2 to hole 1 so that a fiber 3 can be more easily and quickly threaded through hole 1. To grip a fiber 3, a fiber from the gage direction of a testing system is passed over a lower portion of first face 9 of base 2 through the hole 1 or though slot 2 into hole 1. The fiber 3 is then passed over a lower portion of second face 9' and routed back towards the gage direction. Although, the cross-sectional views in FIGS. 1A and 1B and FIGS. 2A and 2B illustrate both sides of the leading fore edge as rounded, it is sufficient for some embodiments that only one side of the leading edge is rounded.

FIG. 3A and cross-sectional view 3B show a detailed view of an alternate fiber routing for the device 20 illustrated in FIGS. 2A and 2B, thus, providing an alternate method of securing a fiber. The base component 2 and clamping magnet 4 are geometrically identical to the device 20 of FIGS. 2A and 2B. However, in this embodiment fiber 3 is further routed along the snubbing surface by passing fiber 3 over a portion of surface 9', through hole 1 over a portion of surface 9, over fore edge 8, and over a portion of surface 9' again. Fiber 3 is then clamped with magnet 4. As used herein, the term "snubbing surface" is a fixed surface around which a fiber is routed, so that when the fiber is loaded in tension there are forces generated between the fiber and the surface that restrain or otherwise suppress the movement of the fiber sufficiently so that the fiber can be tested for mechanical properties, for example a tensile test. The clamping magnet is positioned on edge to ensure that only the fully snubbed fiber is clamped. This embodiment, as compared to the embodiment of FIGS. 1 and 3a, provides a longer snubbing length and therefore is less likely to lead to fiber failure in the grip.

FIG. 4A and cross-sectional view 4B show a detailed view of an alternate fiber routing for the device 10 illustrated in FIGS. 1A and 1B, thus, providing yet another method of securing a fiber. The base component 2 and clamping magnet 4 are geometrically identical to the device 10 of FIG. 1. However, in this embodiment fiber 3 is routed along the snubbing surface by passing fiber 3 over the lower portion of surface 9' through hole 1 over the lower portion of surface 9 and fore edge 8 and over surface 9' again. Fiber 3 is then clamped with magnet 2. The magnet 2 can be positioned on-edge to ensure that only the fully snubbed fiber is clamped. This method as compared to the method illustrated in FIG. 1, also provides a longer snubbing length, for example 360 degrees or one full wrap around a portion of the base 2.

Figure 5B:
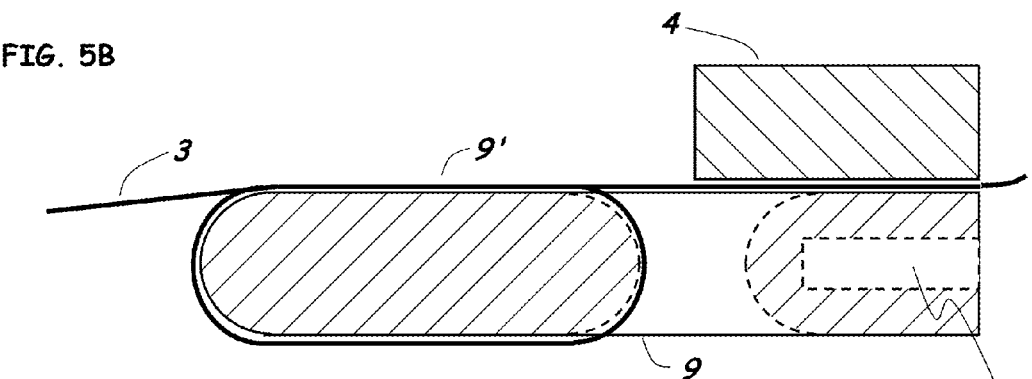
FIG. 5B is a cross-section view of the method of FIG. 5A.
Figure 5A:
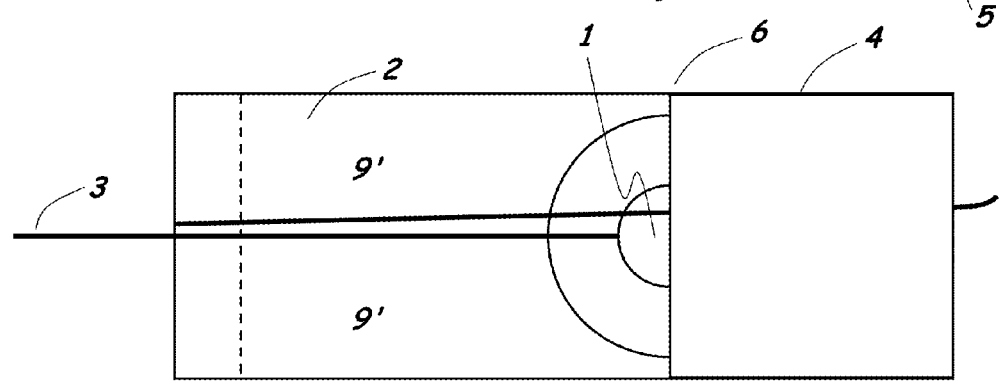
FIG. 5A is a plan view of yet another exemplary method of the present invention.
Figure 6B:
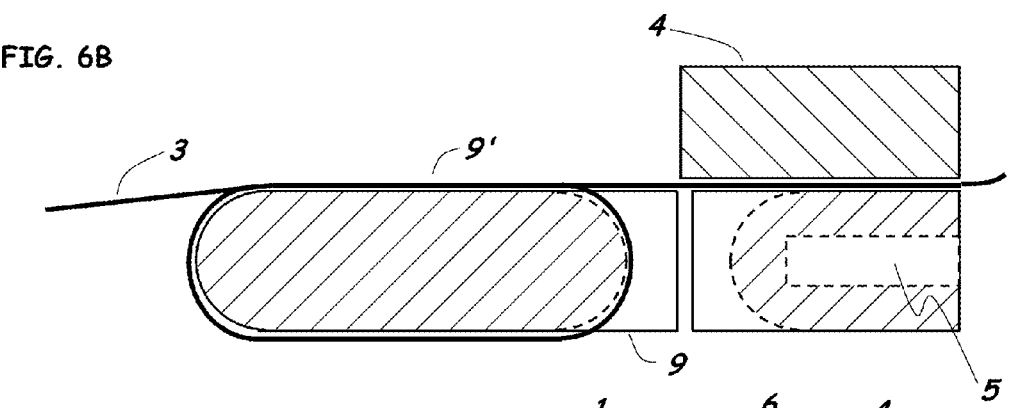
FIG. 6B is a cross-section view of the method of FIG. 6A.
Figure 6A:
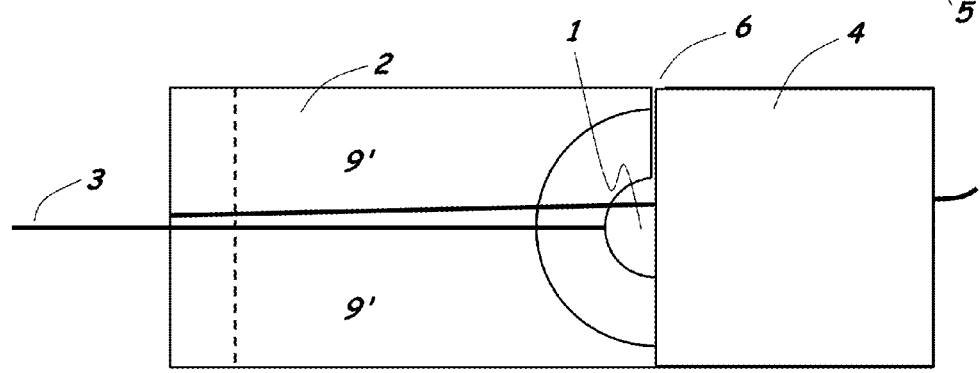
FIG. 6A is a plan view of yet another exemplary method of the present invention.

FIG. 5A and accompanying cross-sectional view 5B shows yet another embodiment of a method of the present invention. The base component and clamping magnet are geometrically identical to the device 20 of FIGS. 2A and 2B. However, in this case, the fiber 3 is routed along an even longer snubbing length than illustrated in the methods of FIGS. 3A and 3B, with the clamping magnet 4 used to clamp the fiber 3 above the threading hole 1. To grip a fiber, a fiber 3 from the gage direction of a testing system is first passed over a lower portion of first face 9', through hole 1 or slot 2 into hole 1, passed over the lower portion of second face 9, over fore edge 8, over the lower portion of surface 9' again and hole 1 and then over the upper portion of surface 9'. Fiber 3 is then clamped to the upper portion of surface 9' with magnet 4. This embodiment utilizes an even longer snubbing length, and is therefore even less likely to lead to fiber failure at the grip.

Further embodiments of this design, assembly and/or method can be easily envisioned including, but not limited to, embodiments utilizing longer or more complex routing paths.

FIGS. 4 illustrate an embodiment of a device of the present invention that includes a slit 6. In this illustrated embodiments, a lateral slit 6 is provided in the base component that extends from one side of the base and connects to the threading hole. This slit 6 does not affect the mechanical performance of the grip or snubbing surfaces, but can greatly simplify loading of a fiber 3 since the fiber end does not need to be passed end-first through the contoured hole 1. Modifications such as rounding the slit or orienting the slit at a different angle are envisioned.

FIG. 7A and a cross-sectional view provided in FIG. 7B show yet another embodiment of the device. In this design, a machined cylindrical hole 17 is machined into the device so that the initial load path of the fiber 3 is more centered relative to the center of the threaded hole 5. This design ensures that the load path of the fiber 3 is more parallel to the load path of the mounting hardware on the load frame of a testing system, such as the testing system described in U.S. Pat. No. 6,679, 124.

It may be desirable to polish the snubbing surfaces of the base component, as well as the faces of the magnet, to eliminate sharp edges or other stress concentrations that may prematurely lead to fiber failure. Rare earth magnets are preferred for the clamping magnet due to their extremely high magnetic forces relative to other magnet types.

It is envisioned that the present gripping device, including clamping magnet, will weigh less than 1 kg and be used to test fibers of diameter 1 mm and smaller. More preferably, the device will weigh less than 100 g and will be used to test fibers of diameter 100 micrometers and smaller. In certain desirable embodiments, devices of the present invention can be used to hold and test fibers having an average diameter of less than 50 micrometers, or more preferably, having an average diameter less than 40 micrometers, or more preferably having an average diameter less than 30 micrometers or even more preferably having an average diameter of less than 25 micrometers.

Figure 8A:
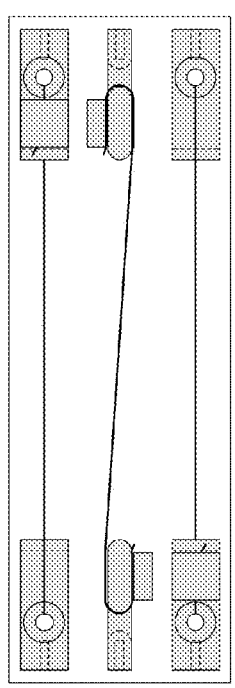
FIG. 8A illustrates an exemplary method of the present invention using a pair of devices illustrated in FIGS. 1A and 1B.
Figure 8B:
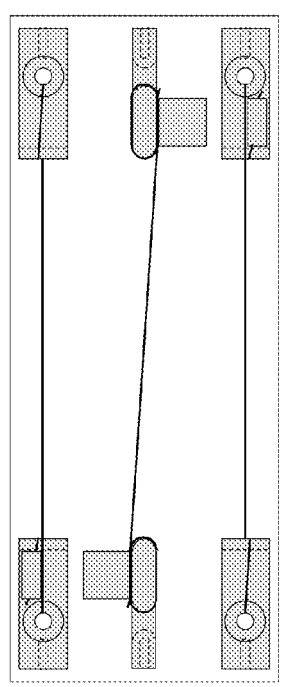
FIG. 8B illustrates another exemplary method of the present invention using a pair of devices of the present invention.
Figure 8C:
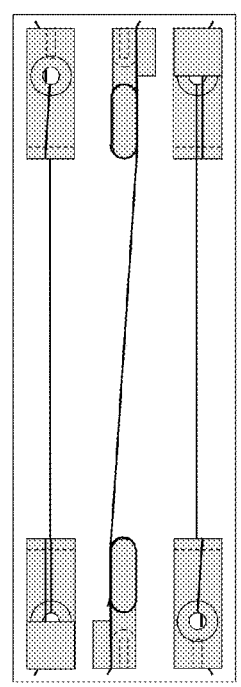
FIG. 8C illustrates yet another exemplary method of the present invention using a pair of devices of the present invention.
Figure 8D:
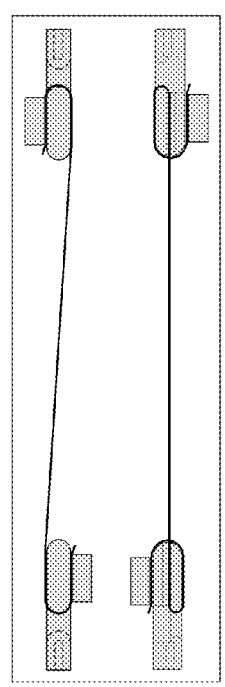
FIG. 8D illustrates still another exemplary method of the present invention using a pair of devices of the present invention.

FIG. 8A illustrates a pair of exemplary devices and clamping method illustrated in FIGS. 1A and 1B that can be used as upper and lower specimen holders in the testing system described in U.S. Pat. No. 6,679,124. FIG. 8B illustrates a pair of exemplary devices of FIGS. 1A and 1B using the clamping method illustrated in FIGS. 4A and 4B providing a longer snubbing length, for example one full wrap around a portion of the base 2 that is less likely to lead to fiber failure in the grip. FIG. 8C illustrates a pair of exemplary devices of FIGS. 1A and 1B using the clamping method illustrated in FIGS. 5A and 5B providing an even longer snubbing length, for example one full wrap around the lower portion of the base 2 and extending to the upper portion of base 2 that even is less likely to lead to fiber failure in the grip. FIG. 8D illustrates a pair of exemplary devices of FIGS. 7A and 7B that provides a load path for the fiber 3 that is more parallel to the load path of the mounting hardware on the load frame of the testing system (not illustrated).

Having described our invention, many modifications thereto will become apparent to those skilled in the art to which it pertains without deviation from the spirit of the invention as defined by the scope of the appended claims.

REFERENCES

1. ASTM Standard D 3822-07. "Standard Test Method for Tensile Properties of Single Textile Fibers." ASTM International, West Conshohocken, Pa. 2007.
2. J. Scott Thornton, Sam R. Allen, and Shawn L. Arnett. "Effect of Gripping Technique on Tensile, Tensile Creep and Tensile Creep-Rupture Results for a High Tenacity Polyester Yarn." In *Grips, Clamps, Clamping Techniques, and Strain Measurement for Testing of Geosynthetics*. P. E. Stevenson, Ed. ASTM STP 1379. ASTM International, West Conshohocken, Pa. p 47-67. 2000.
3. ASTM Standard D 885-04. "Standard Test Methods for Tire Cords, Tire Cord Fabrics, and Industrial Filament Yarns Made from Manufactured Organic-Base Fibers." ASTM International, West Conshohocken, Pa. 2004.

I claim:

1. A clamping device for securing small diameter fibers or small diameter multi-fiber yarns in a mechanical property testing device, comprising:
   a device for testing a mechanical property of a single, small diameter fiber or a small diameter multi-fiber yarn and snubbing surfaces that reduce and moderate fiber load on the single, small diameter fiber or small diameter multi-fiber yarn that is being tested, wherein fiber grippage is provided by magnetic forces.

2. The device of claim 1, where the device weight is 1 kg or less.

3. The device of claim 1 where the snubbing surfaces comprise a magnetizable alloy.

4. The device of claim 1, where the snubbing surfaces are created by machining a rounded hole into a rectangular prism with orthogonal faces, and further rounding any edges that make contact with the fiber.

5. The device of claim 1 for testing the mechanical properties of fibers having an average diameter or less than 100 microns or a multi-fiber yarn having a total average diameter of less than 100 microns wherein the improvement comprises gripping the fiber or the multi-fiber yarn with a magnet.

6. A mechanical property testing device for testing a mechanical property of a single, small diameter fiber or a small diameter multi-fiber yarn, the mechanical property testing device comprising:
   a clamping device for small diameter fibers or small diameter multi-fiber yarns in which snubbing surfaces are used to moderate fiber loads, and fiber grippage is provided by magnetic forces
   where the magnetic gripping forces are provided by an electromagnet.

7. The device of claim 6 where the-device weight is 1 kg or less.

8. The device of claim 6 where the snubbing surfaces comprise a magnetizable alloy.

9. The device of claim 6, where the snubbing surfaces are created by machining a rounded hole into a rectangular prism with orthogonal faces, and further rounding any edges that make contact with the fiber.

10. The device of claim 6 for testing the mechanical properties of fibers having an average diameter or less than 100 microns or a multi-fiber yarn having a total average diameter of less than 100 microns wherein the improvement comprises gripping the fiber or the multi-fiber yarn with a magnet.

11. A mechanical property testing device for testing a mechanical property of a single, small diameter fiber or a small diameter multi-fiber yarn, the mechanical property testing device comprising:
   a clamping device for small diameter fibers or small diameter multi-fiber yarns in which snubbing surfaces are used to moderate fiber loads, and fiber grippage is provided by magnetic forces
   where the snubbing surfaces are created by machining a rounded hole into a rectangular prism with orthogonal faces, and further rounding any edges that make contact with the fiber,
   where all surfaces are polished to a surface roughness of 10 micrometers or smaller, and
   where a slit is machined into the side of the prism to create a direct path from the rounded hole to one of the lateral edges of the prism.

12. The device of claim 11, where the device weight is 1 kg or less or, preferably, 100 g or less.

13. The device of claim 11 where the snubbing surfaces comprise a magnetizable alloy.

14. The device of claim 11, where the snubbing surfaces are created by machining a rounded hole into a rectangular prism with orthogonal faces, and further rounding any edges that make contact with the fiber.

15. The device of claim 11 for testing the mechanical properties of fibers having an average diameter or less than 100 microns or a multi-fiber yarn having a total average diameter of less than 100 microns wherein the improvement comprises gripping the fiber or the multi-fiber yarn with a magnet.

16. A pair of clamping devices for securing small diameter fibers or small diameter multi-fiber yarns in a mechanical property testing device comprising snubbing surfaces used to moderate fiber loads and fiber grippage is provided by magnetic forces, mechanical property testing device comprising
- an upper specimen holder comprising a first snubbing surface and
- a lower specimen holder comprising a second snubbing surface
- wherein the upper specimen holder can be displaced relative to the second specimen holder to test the
- where the snubbing surfaces are created by machining a rounded hole into a rectangular prism with orthogonal faces, and further rounding any edges that make contact with the fiber
- where all surfaces are polished to a surface roughness of 10 micrometers or smaller, and
- where the snubbing surfaces are designed so that the fiber load path is parallel and centered relative to the mounting hole that interfaces the device to an external loading apparatus.

17. The device of claim 16, where the device weight is 1 kg or less or, preferably, 100 g or less.

18. The device of claim 16 where the snubbing surfaces comprise a magnetizable alloy.

19. The device of claim 16, where the snubbing surfaces are created by machining a rounded hole into a rectangular prism with orthogonal faces, and further rounding any edges that make contact with the fiber.

20. The device of claim 16 for testing the mechanical properties of fibers having an average diameter or less than 100 microns or a multi-fiber yarn having a total average diameter of less than 100 microns wherein the improvement comprises gripping the fiber or the multi-fiber yarn with a magnet.

21. An assembly for testing the mechanical properties of fibers having an average diameter or less than 100 microns or a multi-fiber yarn having a total average diameter of less than 100 microns wherein the assembly comprises: a first fiber holder that comprises a first base that comprises a magnetizable alloy and a first magnet for holding a fiber between the first base and the first magnet, and a second fiber holder that comprises a second base that comprises a magnetizable alloy and a second magnet for holding a fiber between the second base and the second magnet.

22. The assembly of claim 21 wherein the first base and the second base each comprises a hole.

23. A device for testing tensile properties of a single fiber having an average diameter of not greater than 100 microns or a multi fiber yarn having an average diameter of not greater than 100 microns comprising: a first fiber holder having a surface that comprises a portion that comprises a ferromagnetic material or other magnetizable alloy; a first magnet for holding one end of a fiber having an average diameter of not greater than 100 microns or multi-fiber yarn having an average diameter of not greater than 100 microns;
- a second fiber holder that comprises a surface that comprises a portion that comprises a ferromagnetic material or other magnetizable alloy; a second magnet for holding another end of a fiber having an average diameter of not greater than 100 microns or multi-fiber yarn having an average diameter of not greater than 100 microns; wherein the surface of the first fiber holder and first magnet are attracted to each other and secure one end of the fiber having an average diameter of not greater than 100 microns or the multi-fiber yarn having an average diameter of not greater than 100 microns and the second fiber holder and second magnet are attracted to each other and secure the other end of the fiber having an average diameter of not greater than 100 microns or multi-fiber yarn having an average diameter of not greater than 100 microns with sufficient force to hold the fiber having an average diameter of not greater than 100 microns or the multi-fiber yarn having an average diameter of not greater than 100 microns during tensile testing.

24. The device as described in claim 23 used in conjunction with a loading frame to characterize the mechanical properties of a fiber.

* * * * *